US007488482B2

(12) United States Patent
Balloul et al.

(10) Patent No.: US 7,488,482 B2
(45) Date of Patent: Feb. 10, 2009

(54) PHARMACEUTICAL COMPOSITIONS FOR TREATING PAPILLOMAVIRUS TUMORS AND INFECTION

(75) Inventors: Jean-Marc Balloul, Lingolsheim (FR); Nadine Bizouarne, Schiltigheim (FR); Marie-Paule Kieny, Strasbourg (FR)

(73) Assignee: Transgene S.A., Strasbourg (FR)

( * ) Notice: Subject to any disclaimer, the term of this patent is extended or adjusted under 35 U.S.C. 154(b) by 25 days.

(21) Appl. No.: 11/522,402

(22) Filed: Sep. 18, 2006

(65) Prior Publication Data

US 2007/0065459 A1 Mar. 22, 2007

Related U.S. Application Data

(62) Division of application No. 09/506,942, filed on Feb. 18, 2000, now Pat. No. 7,118,754, which is a division of application No. 09/043,933, filed as application No. PCT/FR97/01412 on Jul. 29, 1997, now abandoned.

(30) Foreign Application Priority Data

Jul. 30, 1996 (FR) .................................. 96 09584

(51) Int. Cl.
*A61K 39/12* (2006.01)
(52) U.S. Cl. .................................. 424/199.1
(58) Field of Classification Search .............. 424/199.1, 424/204.1
See application file for complete search history.

(56) References Cited

U.S. PATENT DOCUMENTS

| | | | |
|---|---|---|---|
| 5,618,536 A | 4/1997 | Lowy et al. | |
| 5,719,054 A | 2/1998 | Boursnell et al. | |
| 5,855,891 A | 1/1999 | Lowy et al. | |
| 5,866,131 A | 2/1999 | Ramshaw et al. | |
| 5,866,136 A | 2/1999 | Ramshaw et al. | |
| 6,096,869 A | 8/2000 | Stanley et al. | |
| 6,440,422 B1 | 8/2002 | Sutter et al. | |
| 6,884,786 B1 * | 4/2005 | Kieny et al. ............... | 514/44 |
| 7,118,754 B1 * | 10/2006 | Balloul et al. ............ | 424/199.1 |

FOREIGN PATENT DOCUMENTS

| | | |
|---|---|---|
| WO | WO 90/10459 | 9/1990 |
| WO | WO 92/16636 | 10/1992 |
| WO | WO 93/00436 | 1/1993 |
| WO | WO 93/02184 | 2/1993 |
| WO | WO 94/23037 | 10/1994 |
| WO | WO 94/24267 | 10/1994 |
| WO | WO 96/00583 | 1/1996 |
| WO | WO 96/11274 | 4/1996 |
| WO | WO 96/29091 | 9/1996 |

OTHER PUBLICATIONS

Zhou et al., Virology, 185:241-257, 1991.
Heck et al., PNAS USA, 89:4442-4446, 1992.
Galloway, 1994, "Human Papillomavirus Vaccines: A Warty Problem", Infectious Agents and Disease, 3:187-193.
Hines et al., 1995, "Prospects for a Vaccine against Human Papillomavirus", Obstectrics and Gynecology, 86(5):860-866.
Gajewski, 1996, "B7.1 but not B7.2 Efficiently Costimulates CD8+ T Lymphocytes in the P815 Tumor System in vitro", The Journal of Immunology, 156:465-472.
Crook et al., "Degradation of P53 can be Targeted by HPV E6 Sequences Distinct from those Required for P53 Binding and Transactivation", Cell, 1991, 67:547-556.
International Search Report dated Nov. 19, 1997.
Meyer et al. 1991. Mapping of deletions in the genome of the highly attenuated vaccinia virus MVA and their influence on virulence. Journal of General Virology. vol. 72, pp. 1031-1038.
Borysiewicz et al. The Lancet. Jun. 1, 1996; 347: 1523-1527.
Lin et al. (Virology. 1992; 187: 612-619.
Munger et al., 1989, "Complex Formation of Human Papillomavirus E7 Proteins with the Retinoblastoma Tumor Suppressor Gene Product", The EMBO Journal, 8: 4099-4105.
Bubenik et al., International Journal of Oncology, Mar. 1996; 8: 477-481.
Baltz, American Journal of Health-System Pharmacy. 1995; 52: 2574-2585.
Hagensee et al., Journal of Virology, 1993; 67 (1): 315-322.
Bash et al., Journal of Immunotherapy. 1993; 14: 269-272.

\* cited by examiner

*Primary Examiner*—Ali R. Salimi
(74) *Attorney, Agent, or Firm*—Buchanan, Ingersoll & Rooney, P.C.

(57) ABSTRACT

A pharmaceutical composition for treating or preventing a papillomavirus infection or tumour, including, as the therapeutical agents, a polypeptide from an early region and a polypeptide from a late region of a papillomavirus, optionally combined-with a polypeptide having immunostimulatory activity or a polypeptide from an early or late region of a papillomavirus and a polypeptide having immunostimulatory activity, or alternatively, a recombinant vector containing inserted DNA fragments coding for the above-mentioned polypeptide combinations.

15 Claims, 3 Drawing Sheets

SEQUENCE LISTING

```
<160> NUMBER OF SEQ ID NOS: 16

<210> SEQ ID NO 1
<211> LENGTH: 36
<212> TYPE: DNA
<213> ORGANISM: Human papillomavirus

<400> SEQUENCE: 1
tctgagctgt catttaattg agttgtctct ggttgc                            36

<210> SEQ ID NO 2
<211> LENGTH: 32
<212> TYPE: DNA
<213> ORGANISM: Human papillomavirus

<400> SEQUENCE: 2
tgtccagatg tctttgcagt ggcttttgac ag                                32

<210> SEQ ID NO 3
<211> LENGTH: 35
<212> TYPE: DNA
<213> ORGANISM: Homo sapiens

<400> SEQUENCE: 3 tcagccctg aattctgcgg acactgttat acagg                              35

<210> SEQ ID NO 4
<211> LENGTH: 33
<212> TYPE: DNA
<213> ORGANISM: Homo sapiens

<400> SEQUENCE: 4
ttgaccctaa agatctgaag ccatgggcca cac                               33

<210> SEQ ID NO 5
<211> LENGTH: 32
<212> TYPE: DNA
<213> ORGANISM: Vaccinia virus

<400> SEQUENCE: 5
```

```
ggggggggaat tcagtaaact tgactaaatc tt                                32
```

<210> SEQ ID NO 6
<211> LENGTH: 39
<212> TYPE: DNA
<213> ORGANISM: Vaccinia virus

<400> SEQUENCE: 6

```
ggggggggat ccgagctcac cagccaccga aagagcaat                         39
```

<210> SEQ ID NO 7
<211> LENGTH: 32
<212> TYPE: DNA
<213> ORGANISM: Vaccinia virus

<400> SEQUENCE: 7

```
ggggggggat ccggaaagtt ttataggtag tt                                32
```

<210> SEQ ID NO 8
<211> LENGTH: 30
<212> TYPE: DNA
<213> ORGANISM: Vaccinia virus

<400> SEQUENCE: 8

```
gggggggaat tctttgtatt tacgtgaacg                                   30
```

<210> SEQ ID NO 9
<211> LENGTH: 78
<212> TYPE: DNA
<213> ORGANISM: Vaccinia virus

<400> SEQUENCE: 9

```
cttatacagg gcgtacactt tcccttctca atctctctcg agttgtattt attttcattt   60
tttaagtata gaataaaa                                                78
```

<210> SEQ ID NO 10
<211> LENGTH: 86
<212> TYPE: DNA
<213> ORGANISM: Vaccinia virus

<400> SEQUENCE: 10

```
agcttttat tctatactta aaaatgaaa ataaatacaa ctcgagagag attgagaagg     60
gaaagtgtac gccctgtata aggtac                                       86
```

<210> SEQ ID NO 11
<211> LENGTH: 39
<212> TYPE: DNA
<213> ORGANISM: Vaccinia virus

<400> SEQUENCE: 11

```
atggtaccga attccatcta ccaattcatc caacaacat                         39
```

<210> SEQ ID NO 12
<211> LENGTH: 41
<212> TYPE: DNA
<213> ORGANISM: Vaccinia virus

<400> SEQUENCE: 12

```
ggctgcagga tccgagctca tcatgacgtc ctctgcaatg g                      41
```

<210> SEQ ID NO 13
<211> LENGTH: 32

-continued

```
<212> TYPE: DNA
<213> ORGANISM: Vaccinia virus

<400> SEQUENCE: 13
ggggggggat cctgtgaatc atccattcca ct                                32

<210> SEQ ID NO 14
<211> LENGTH: 33
<212> TYPE: DNA
<213> ORGANISM: Vaccinia virus

<400> SEQUENCE: 14 ggggggaat tcgttactaa attgcaagga aat                                33

<210> SEQ ID NO 15
<211> LENGTH: 69
<212> TYPE: DNA
<213> ORGANISM: Vaccinia virus

<400> SEQUENCE: 15
ctcaagtcag tgttgagatg atgctttgac aactcgagtt tattttcatt ttttaagtat   60
agaataaaa                                                          69

<210> SEQ ID NO 16
<211> LENGTH: 77
<212> TYPE: DNA
<213> ORGANISM: Vaccinia virus

<400> SEQUENCE: 16
agctttttat tctatactta aaaaatgaaa ataaactcga gttgtcaaag catcatctca   60
acactgactt gaggtac                                                 77
```

PHARMACEUTICAL COMPOSITIONS FOR TREATING PAPILLOMAVIRUS TUMORS AND INFECTION

Figure 1:
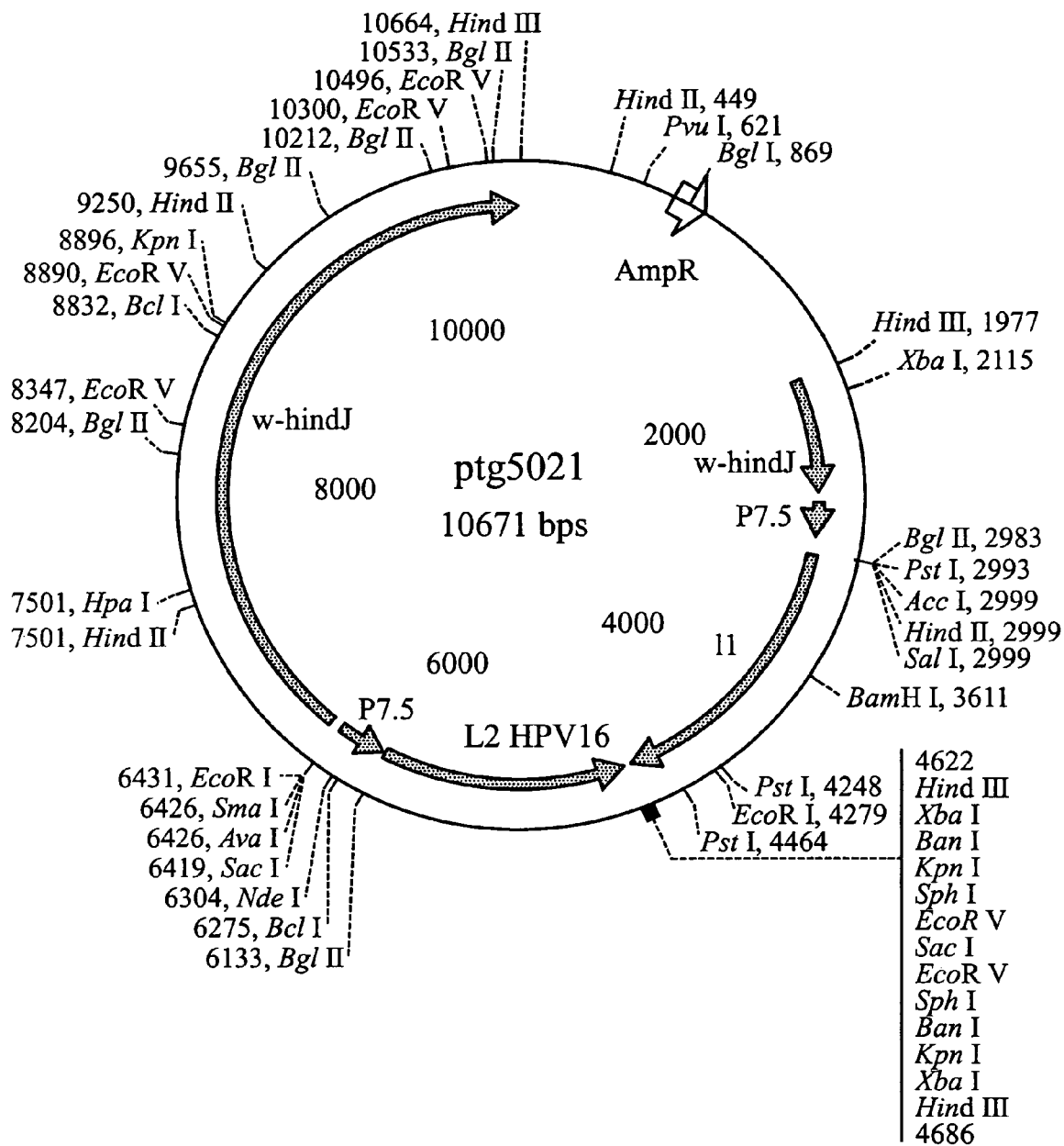

This is a divisional of application Ser. No. 09/506,942, filed Feb. 18, 2000, now U.S. Pat. No. 7,118,754, which is a divisional of Ser. No. 09/043,933, filed Mar. 30, 1998, abandoned, which is a 371 application of International Application No. PCT/FR97/01412, filed Jul. 29, 1997, which claims priority to FR 96 09584, filed Jul. 30, 1996, all of which are incorporated herein by reference.

The subject of the present invention is a pharmaceutical composition intended for the treatment or prevention of lesions associated with papillomaviruses and more particularly with human papillomaviruses (HPV) types 16, 18, 31, 33 and 45.

Papillomaviruses are DNA viruses possessing a circular genome of about 7900 base pairs surrounded by a protein capsid. A number of bovine (BPV) and human (HPV) papillomavirus types have been identified and their genome sequenced (Pfister, 1987, in *The papoviridae: The Papillomaviruses* (Salzman and Howley publishing) Plenum Press, New York, p 1-38). It comprises an early region and a late region. The late region contains two reading frames L1 and L2 which code for the major components of the capsid. The early region contains at least the reading frames E1, E2, E4, E5, E6 and E7. The E1 and E2 expression products regulate viral replication and the expression of the viral genes whereas those of the E5, E6 and E7 regions are involved in the processes of oncogenic transformation of infected cells. Indeed, it has been shown experimentally that the BPV-1 E5 protein can transform cells in vitro (Schlegel et al., 1986, Science 233, 464-467). The BPV-1 E6 and HPV-16 E7 proteins are involved in the induction and maintenance of oncogenic transformation. The transforming power of E7 has been demonstrated for HPV-16 and HPV-18 (Kanda et al., 1988, J. Virol. 62, 610-613; Vousden et al., 1988, Oncogene Res. 3, 1-9; Bedell et al., 1987, J. Virol. 61, 3635-3640). No function has been demonstrated in E4.

In man, HPVs are associated with pathologies ranging from benign infection of the skin to warts and to malignant tumors. These viruses are highly specific for the epithelium of the epidermis of the genital, oral and respiratory tracts. The epidemiological data strongly suggest the role of certain strains in cancer of the neck of the uterus and of the lower pathologies, in particular HPV-16 and -18 and to a lesser degree HPV-31, -33 and -45. Cancer of the neck of the uterus is the second cause of female cancer worldwide. According to the WHO, 460,000 new cases are recorded each year, of which at least 200,000 cases are clearly associated with HPV. A series of studies demonstrates the transforming role of these viruses, their specific integration into the genome of neoplastic cells, their gene activity in cancer cells and the importance of the expression of the E6 and E7 early genes in maintaining the malignant phenotype of HPV-positive neoplastic cells (Monsenego, J. Impact Medecin, Mar. 11, 1994).

Pathological conditions associated with HPV viruses give rise to a therapeutic problem on account of their persistent and recurrent nature. Many approaches have already been used in the treatment of these diseases, such as surgery, chemotherapy, antiviral agents and immunotherapy.

In this regard, European Patent EP 0,462,187 describes a vaccination approach using papillomavirus early genes to establish immunity against tumors resulting from the integration of the HPV genome into the cellular DNA and in which the capsid proteins are no longer expressed. Application WO 93/02184 teaches a therapeutic approach based on the use of the capsid antigens as immunogenic agents. These documents do not suggest the possibility of combining the preventive effect offered by the early polypeptides and the curative effect conferred by the late polypeptides of papillomaviruses to generate compositions suited to all the serious pathological conditions caused by HPVs. Moreover, during the past few years, it has been proposed to use polypeptides having immunostimulatory activity with the aim of activating the T cells with a result which is beneficial to a greater or lesser degree depending on the pathological conditions targeted (see for example WO 96/11279).

The present invention relates more precisely to a preparation based on a mixture of antigens from the early and late regions of a papillomavirus or a vector expressing them simultaneously, with the aim of establishing lasting immunity against infected cells. The candidate vaccines provided within the framework of the present invention can be used for preventive purposes (immunoprophylaxy) to limit the development or propagation of viral infection to the neighboring tissues or for curative purposes (immunotherapy) to prevent or reduce tumor progression in infected patients. The use of the capsid antigens will induce the production of antibodies against the antigenic epitopes located at the surface of the viral particles, preventing the infection from becoming established for a lengthy period. The use of the early proteins will make it possible to induce immunity against the cells infected after integration of the viral DNA.

The present invention also provides a preparation combining a polypeptide from a papillomavirus and an immunostimulatory molecule. One of the advantages of such a composition is that it combines the specific immunity induced by the viral antigens and the aspecific immunity induced by the immunostimulatory molecule designed to reinforce the specific response.

The aim of the present invention is to make available to the public pharmaceutical compositions allowing the treatment of HPV infections and more particularly serious pathologies such as cancer of the neck of the uterus, having improved efficacy compared with the prior art compositions.

Accordingly, the subject of the present invention is a pharmaceutical composition intended for the treatment or prevention of a papillomavirus infection or tumor, which comprises, as therapeutic agents:

(1) at least one polypeptide from the early region of a papillomavirus and at least one polypeptide from the late region of a papillomavirus, (2) at least one polypeptide from the early region of a papillomavirus, at least one polypeptide from the late region of a papillomavirus and at least one polypeptide having imunostimulatory activity, or (3) at least one polypeptide from an early or late region of a papillomavirus and at least one polypeptide having immunostimulatory activity.

In general, the term polypeptide refers to all or part of the native polypeptide, to a chimeric polypeptide resulting from the fusion of sequences of different origins or to a variant characterized by at least one mutation (deletion, insertion and/or substitution) of an amino acid. More particularly, a polypeptide in use within the framework of the present invention has, in particular, an amino acid sequence whose degree of similarity with the sequence of the native protein is greater than 75%, advantageously greater than 85% and, preferably, greater than 95%. The degree of similarity can be easily calculated with the aid of an appropriate computer program or by aligning the sequences so as to obtain the maximum degree of homology and by counting the number of positions in which the amino acids of the two sequences are found to be identical in relation to the total number of positions. The sequence of the HPV-16 and HPV-18 genomes is disclosed in Genebank with accession numbers K02718 and X05015 respectively.

As recalled earlier, the genome of viruses of the papillomavirus family, in-particular BPV and HPV, codes for at least 8 polypeptides, two late polypeptides L1 and L2 comprising the viral capsid and 6 early polypeptides (E1, E2, E4, E5, E6 and E7) involved in the regulation and maintenance of the viral genome and in the transformation of the infected cells.

Although all the early proteins of a papillomavirus can be used within the framework of the present invention, the choice is made advantageously to use a polypeptide derived from the E6 protein, from the E7 protein or from the E6 and E7 proteins. It may be advantageous to use a nononcogenic variant mutated at the level of the regions involved in the process of transformation of the infected cells. Such variants are described in the literature (Munger et al., 1989, EMBO J. 8, 4099-4105; Crook et al., 1991, Cell 67, 547-556; Heck et al., 1992, Proc. Natl. Acad. Sci. USA 89, 4442-4446; Phelps et al., 1992, J. Virol. 66, 2418-2427).

A preferred polypeptide from the late region of a papillomavirus is derived from the L1 protein, from the L2 protein or from the L1 and L2 proteins.

According to the particularly advantageous embodiments (2) and (3), a composition according to the invention also comprises a polypeptide having an immunostimulatory activity. "Immunostimulatory" is understood to mean the capacity to stimulate a humoral immune is response by activating the B lymphocytes so as to amplify the production of antibodies directed against the papillomavirus antigens or to stimulate a cell-mediated immune response by activating the T lymphocytes so as to trigger a significant cytotoxic response against tumor cells or cells infected by a papillomavirus. As a guide, the immunostimulation can be evaluated in an animal model (by comparing the level of rejection in an animal into which a tumor expressing the target antigen has been transplanted, this being in the presence and in the absence of the immunostimulant). More generally, the means for demonstrating an immunostimulation are indicated in Roitt (in *Immunology*, 4th edition, Moby Ltd).

It is possible to use a native immunostimulatory molecule as found in a mammal, and, in particular, in man, a portion thereof, a chimeric molecule obtained from the fusion of sequences of various origins or a mutant, provided, however, the immunostimulatory function is preserved. Among all the molecules which can be envisaged, a polypeptide consisting of or derived from interleukin-2, interleukin-7, interleukin-12 and co-adhesion molecules B7.1 and B7.2 will be preferably used, interleukin-2 and the molecule B7.1 being particularly preferred within the framework of the present invention.

A preferred composition according to the invention comprises:
(1) a polypeptide from the E6 region, a polypeptide from the E7 region, a polypeptide from the L1 region and a polypeptide from the L2 region of a papillomavirus,
(2) a polypeptide from the E6 region, a polypeptide from the E7 region of a papillomavirus and a polypeptide derived from interleukin-2,
(3) a polypeptide from the E6 region, a polypeptide from the E7 region of a papillomavirus and a polypeptide derived from the molecule B7.1,
(4) a polypeptide from the E6 region, a polypeptide from the E7 region of a papillomavirus, a polypeptide derived from the molecule B7.1 and a polypeptide derived from interleukin-2,
(5) a polypeptide from the E6 region, a polypeptide from the E7 region, a polypeptide from the L1 region, a polypeptide from the L2 region of a papillomavirus and a polypeptide derived from interleukin-2,
(6) a polypeptide from the E6 region, a polypeptide from the E7 region, a polypeptide from the L1 region, a polypeptide from the L2 region of a papillomavirus and a polypeptide derived from the molecule B7.1, or
(7) a polypeptide from the E6 region, a polypeptide from the E7 region, a polypeptide from the L1 region, a polypeptide from the L2 region of a papillomavirus, a polypeptide derived from the molecule B7.1 and a polypeptide derived from interleukin-2.

Given the observations recalled above on the incidence of infection by some HPV types in the cases of cancer of the neck of the uterus, a composition according to the invention comprises a polypeptide from a risk-carrying papillomavirus of the HPV-16, HPV-18, HPV-31, HPV-33 and/or HPV-45 type, and in particular from the HPV-16 virus. Of course, in the case where the composition includes several papillomavirus antigens, they may be of common or different origin.

In general, a polypeptide from a papillomavirus or having an immunostimulatory activity can be produced by the conventional methods of chemical synthesis or alternatively by recombinant DNA techniques (see for example Maniatis et al., 1989, *Laboratory Manual*, Cold Spring Harbor, Laboratory Press, Cold Spring Harbor, N.Y.). More particularly, a method of preparation comprises the act of culturing a cell transformed with a DNA fragment coding for the polypeptide in question so as to generate a producing cell and the act of harvesting said polypeptide from the culture. The producing cell may be of any origin and without limitation, a bacterium, a yeast or alternatively a mammalian cell, insofar as the DNA fragment considered is either integrated into its genome or integrated into an appropriate expression vector capable of replicating. Of course, the DNA fragment is placed under the control of transcriptional and translational signals allowing its expression in the producing cell. Expression vectors and control signals are known to persons skilled in the art.

The present invention also relates to a pharmaceutical composition intended for the treatment or prevention of a papillomavirus infection or tumor, which comprises, as therapeutic agent(s), one or more recombinant vectors into which there are inserted DNA fragments coding for:
(1) at least one polypeptide from the early region of a papillomavirus and at least one polypeptide from the late region of a papillomavirus,
(2) at least one polypeptide from the early region of a papillomavirus, at least one polypeptide from the late region of a papillomavirus and at least one polypeptide having an immunostimulatory activity, or
(3) at least one polypeptide from an early or late region of a papillomavirus and at least one polypeptide having an immunostimulatory activity;

said DNA fragments being placed under the control of the elements necessary for their expression in a host cell or organism.

According to this alternative which is in fact preferred, the therapeutic agent is a vector into which there are inserted the DNA fragments coding for the polypeptides from a papillomavirus or immunostimulants as defined above. This type of composition has the advantage of cheap production and high stability under a variety of environmental conditions. In particular, the preservation conditions are less constraining.

The DNA fragments coding for a polypeptide from a papillomavirus can be obtained by cloning, by PCR (Polymerase Chain Reaction) or by chemical synthesis according to the conventional techniques commonly used starting with positive papillomavirus cells obtained from patients or from collections.

The gene coding for a polypeptide having immunostimulatory activity can also be isolated according to standard techniques from the genome of a cell (genomic type) or from the messenger RNAs of a cell in which it is expressed (complementary DNA type). Moreover, the gene in question can code for (i) a soluble molecule, which is either intracellular or secreted into the external medium, or (ii) a molecule anchored in the membrane and therefore present at the surface of the cells expressing it.

A preferred recombinant vector within the framework of the invention is a viral vector into whose genome there have been inserted the abovementioned DNA fragments so as to allow their transfer and their expression in a host cell or organism. A viral vector which can be used within the framework of the present invention may be derived in particular from a poxvirus, an adenovirus, a retrovirus, a herpesvirus or an adeno-associated virus. Advantageously, it may be a non-integrative vector having an attenuated virulence. Such vectors, as well as the techniques for preparing them, are known to persons skilled in the art.

In the case where an adenoviral vector is used, there will be preferably used a vector which is non-replicative by virtue of the deletion of regions essential for replication and, in particular, of the majority of the E1 region so as to avoid its propagation within the host organism or the environment. It goes without saying that other regions of the adenoviral genome can be modified or deleted insofar as the defective essential functions are trans-complemented. A preferred adenoviral vector according to the invention will retain the sequences essential for encapsidation, namely the 5' and 3' ITRs (Inverted Terminal Repeat) and the encapsidation region. The various adenoviral vectors as well as the techniques for preparing them are conventional and are described in Graham and Prevect (1991, in *Methods in Molecular Biology*, vol 7, p 109-128; Ed: E. J. Murey, The Human Press Inc.) and in international application WO 94/28152. If a retrovirus is used, the LTRs (Long Terminal Repeat) and the encapsidation sequences will be retained (see for example Naviaux and Verma, 1992, Current Opinion in Biotechnology 3, 540-547).

According to an advantageous embodiment, a recombinant viral vector according to the invention is derived from a poxvirus and, in particular, from an avian poxvirus such as the canarypox virus, a fowlpox virus or a vaccinia virus, the latter being preferred. Among all the vaccinia viruses which can be envisaged within the framework of the present invention, the Copenhagen, Wyeth and modified Ankara (MVA for Modified Vaccinia Ankara Virus) strains are preferably chosen. The general conditions for obtaining a vaccinia virus capable of expressing a heterologous gene are taught in European Patent EP 83 286 and application EP 206 920. As for the MVA virus, it is more-particularly described in (Mayr et al., 1975, Infection 3, 6-14; Sutter and Moss, 1992, Proc. Natl. Acad. Sci. USA 89, 10847-10851).

Of course, in the framework of the present invention, the DNA fragments are placed under the control of the elements necessary for their expression. These include the appropriate elements for regulation of transcription as well as signals for initiation and termination of translation. The promoter is of particular importance. In general, use will be made of a promoter which is functional in the host organism or cell which it is desired to treat and which is suited to the vector used. In addition, it can be modified so as to contain regulatory sequences, for example an element for activating transcription or sequences responding to certain cellular signals. In this regard, it may be advantageous to use a tissue-specific promoter since the lesions associated with papillomaviruses are located at the level of the genital tracts, or a promoter responding to tumor-specific signals (for example which is activated in the presence of growth factors which are generally overexpressed by tumor cells) so as to limit the expression to tumor cells alone.

Among the promoters which can be envisaged within the framework of the invention, there may be mentioned the SV40 (Simian Virus 40) promoters, the HMG (Hydroxy-Methyl-Glutaryl-coenzyme A) promoters, the TK (Thymidine Kinase) promoters, the CMV (cytomegalovirus) promoters, the RSV (Rous Sarcoma Virus) promoters, the adenovirus MLP (Major Late Promoter) promoters which are suited to adenoviral vectors and the Mo-MLV (Moloney Murine Leukemia Virus) LTR promoters which are more specific to retroviral vectors. When the vector is derived from a poxvirus, the promoter will be preferably the promoter of a gene of the poxvirus used, for example the promoter of the gene coding for the protein 7.5K, H5R, TK or K1L of the vaccinia virus. They are described in the literature and can be cloned from the viral genome by conventional techniques.

Moreover, the elements necessary for the expression may also comprise sequences enhancing the expression or maintenance in the host cell (intron, signal sequence, sequence for termination of transcription, site of initiation of translation, sequences modifying the presentation of the polypeptide to the cells of the host's immune system and the like). However, for a vector derived from a poxvirus, the use of introns will be avoided.

A composition according to the invention can be obtained either with several recombinant vectors, each expressing a given polypeptide, or with a single vector expressing the DNA fragments corresponding to the chosen polypeptides placed under the control of independent or common elements. According to the latter option, there may be used sequences which make it possible to initiate translation internally (IRES) or fusions of the different genes in phase.

The general conditions for obtaining a recombinant vector in use in the present invention are widely described in the state of the art. As regards a poxviral vector, reference may be made to European Patent EP 83 286 the content of which is incorporated herein by reference. These conditions are applicable to the other viruses acceptable as a vector, which possess a non-essential genomic region into which the expression units may be incorporated. Of course, they may be inserted in the same locus or in a different locus. For example, when the Copenhagen strain of a vaccinia virus is used, the preferred site of insertion is the TK locus and/or the K1L locus. The insertion at the level of the viral TK gene has the effect of inactivating it and thus of facilitating the selection of the recombinants. In the context of the MVA strain of a vaccinia virus, the insertion of the immunostimulatory and papillomavirus genes can be carried out within one of the excisions I to VI and, preferably, the excision zone II or III (Meyer et al., 1991, J. Gen. Virol. 72, 1031-1038; Sutter et al., 1994, Vaccine 12, 1032-1040).

In accordance with the objectives pursued by the present invention, a recombinant vector may, in addition, comprise a unit for expression of a selectable marker gene in order to facilitate the steps for isolating and purifying the recombinant virus. There may be mentioned in particular the Neo gene which confers resistance to the antibiotic G418, the pac gene for resistance to puromycin, the herpes simplex virus type 1 (HSV-1) TK gene which confers sensitivity to certain nucleoside analogs such as ganciclovir or acyclovir, the bacterial genes LacZ coding for β-galactosidase and gus A coding for β-glucuronidase. The latter two enzymatic markers make it possible to pick out the recombinant viruses by staining in the presence of the substrates X-Gal (5-bromo-4-chloro-3-indolyl β-D-galactopyranoside) and XglcA (5-bromo-6-chloro-3-indolyl β-D-glucoronide) respectively.

A pharmaceutical composition according to the invention for the treatment or prevention of a papillomavirus infection or tumor comprises one or more recombinant vectors derived from the Copenhagen or MVA strain of a vaccinia virus into which there are inserted:

(1) a DNA fragment coding for the E6 protein of a papillomavirus, a DNA fragment coding for the E7 protein of a papillomavirus and a DNA fragment coding for the molecule B7.1, (2) a DNA fragment coding for the E6 protein of a papillomavirus, a DNA fragment coding for the E7 protein of a papillomavirus and a DNA fragment coding for interleukin-2, (3) a DNA fragment coding for the E6 protein of a papillomavirus, a DNA fragment coding for the E7 protein of a papillomavirus, a DNA fragment coding for the molecule B7.1 and a DNA fragment coding for interleukin-2, (4) a DNA fragment coding for the E6 protein of a papillomavirus, a DNA fragment coding for the E7 protein of a papillomavirus, a DNA fragment coding for the L1 protein of a papillomavirus and a DNA fragment coding for the L2 protein of a papillomavirus, (5) a DNA fragment coding for the E6 protein of a papillomavirus, a DNA fragment coding for the E7 protein of a papillomavirus, a DNA fragment coding for the L1 protein of a papillomavirus, a DNA fragment coding for the L2 protein of a papillomavirus and a DNA fragment coding for the molecule B7.1, (6) a DNA fragment coding for the E6 protein of a papillomavirus, a DNA fragment coding for the E7 protein of a papillomavirus, a DNA fragment coding for the L1 protein of a papillomavirus, a DNA fragment coding for the L2 protein of a papillomavirus and a DNA fragment coding for interleukin-2, or (7) a DNA fragment coding for the E6 protein of a papillomavirus, a DNA fragment coding for the E7 protein of a papillomavirus, a DNA fragment coding for the L1 protein of a papillomavirus, a DNA fragment coding for the L2 protein of a papillomavirus, a DNA fragment coding for the molecule B7.1 and a DNA fragment coding for interleukin-2.

On the other hand, a pharmaceutical composition according to the invention more particularly intended for immunoprophylaxy comprises one or more recombinant vectors derived from the Copenhagen or MVA strain of a vaccinia virus, into which there are inserted:

(1) a DNA fragment coding for the L1 protein of a papillomavirus, a DNA fragment coding for the L2 protein of a papillomavirus and a DNA fragment coding for the molecule B7.1, (2) a DNA fragment coding for the L1 protein of a papillomavirus, a DNA fragment coding for the L2 protein of a papillomavirus and a DNA fragment coding for interleukin-2, or (3) a DNA fragment coding for the L1 protein of a papillomavirus, a DNA fragment coding for the L2 protein of a papillomavirus, a DNA fragment coding for interleukin-2 and a DNA fragment coding for the molecule B7.1.

A composition according to the invention can be prepared according to methods known in the field of vaccines and the applicable doses may vary within a wide range. They depend in particular on the polypeptides and on the virus used, the pathological condition to be treated, the condition of the patient and other parameters which may be evaluated by the clinician. However, in general, the dose of virus per kilo will be from $10^4$ to $10^{11}$, advantageously from $10^6$ to $10^{10}$ and, preferably, from $10^7$ to $10^9$ plaque forming units (pfu) when the therapeutic agent is a viral vector and from 0.05 to 500 mg, advantageously from 0.5 to 200 mg and, preferably, from 1 to 100 mg when the therapeutic agent is of polypeptide origin.

A composition according to the invention can be administered by any conventional route of administration, in particular by the intravenous, intramuscular, subcutaneous or subepithelial route, or alternatively by scarification. In the case of an accessible tumor, it is also possible to use direct injection into the site or in the vicinity of the tumor or to use topical application. As a vaccine, a composition according to the invention can be administered according to practices which are common in the field, for example as a single dose or a dose repeated once or several times after a certain time interval. On the other hand, in the context of a curative treatment, it can be administered frequently for a period which is sufficient for the treatment to be effective. When the therapeutic agent is a viral vector, this virus is preferably in a live form. In the case of a poxviral vector, the use of an attenuated strain such as the thymidine kinase negative Copenhagen strain or MVA strain will be preferred. Finally, a recombinant viral vector can be attenuated by an appropriate chemical treatment known to persons skilled in the art. However, injecting a killed recombinant vector can also be envisaged.

According to a preferred embodiment, a pharmaceutical composition according to the invention comprises a therapeutically effective quantity of a recombinant vector in combination with a pharmaceutically acceptable carrier. The carrier is chosen so as to allow its administration by injection into humans or into animals. It may also comprise a vehicle, a diluent and/or an adjuvant and may be provided in liquid or freeze-dried form.

The present invention also relates to a pharmaceutical composition according to the invention, as a medicament for the treatment or prevention of cancer of the neck of the uterus, of a dysplasia of the neck of low grade and of a papillomavirus infection.

Finally, the present invention also relates to a method of treating or preventing the abovementioned pathological conditions, according to which a pharmaceutically effective quantity of a mixture of polypeptide or of a recombinant vector in use in the present invention is administered to an individual needing such a treatment.

The present invention is illustrated by reference to the following figures.

FIG. 1 is a diagrammatic representation of the vector pTG5021 allowing the transfer, to the TK locus of the Copenhagen vaccinia, of the HPV-16 late genes L1 and L2 placed under the control of the promoter p7.5K, the two cassettes being in opposite orientation relative to each other.

Figure 2:
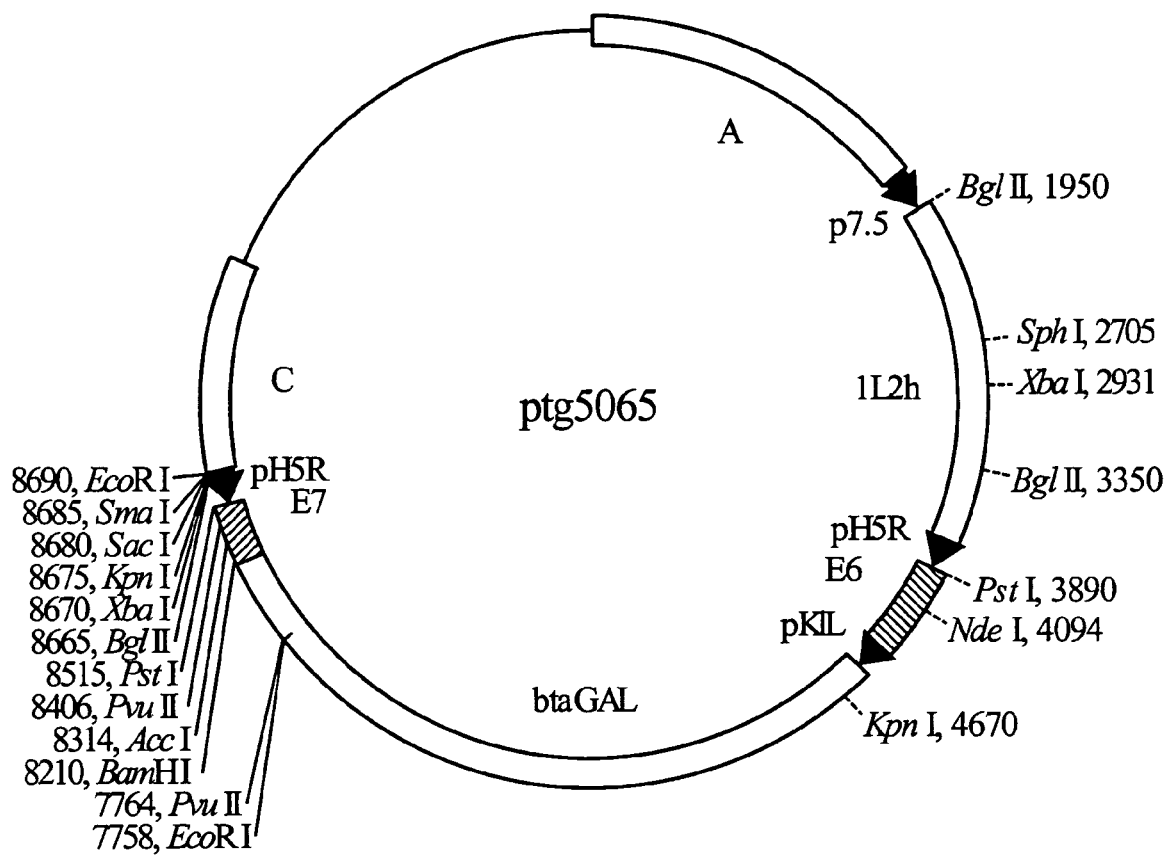

FIG. 2 is a diagrammatic representation of the vector pTG5065 allowing the transfer, to the K1L locus of the Copenhagen vaccinia, of the HPV-16 early genes E6 and E7 placed under the control of the promoter pH5R (the two cassettes being in opposite orientation relative to each other), of the human IL-2 (IL2h) gene placed under the control of the promoter p7.5K and of the marker gene LacZ (btaGAL) placed under the control of the promoter pK1L.

Figure 3:
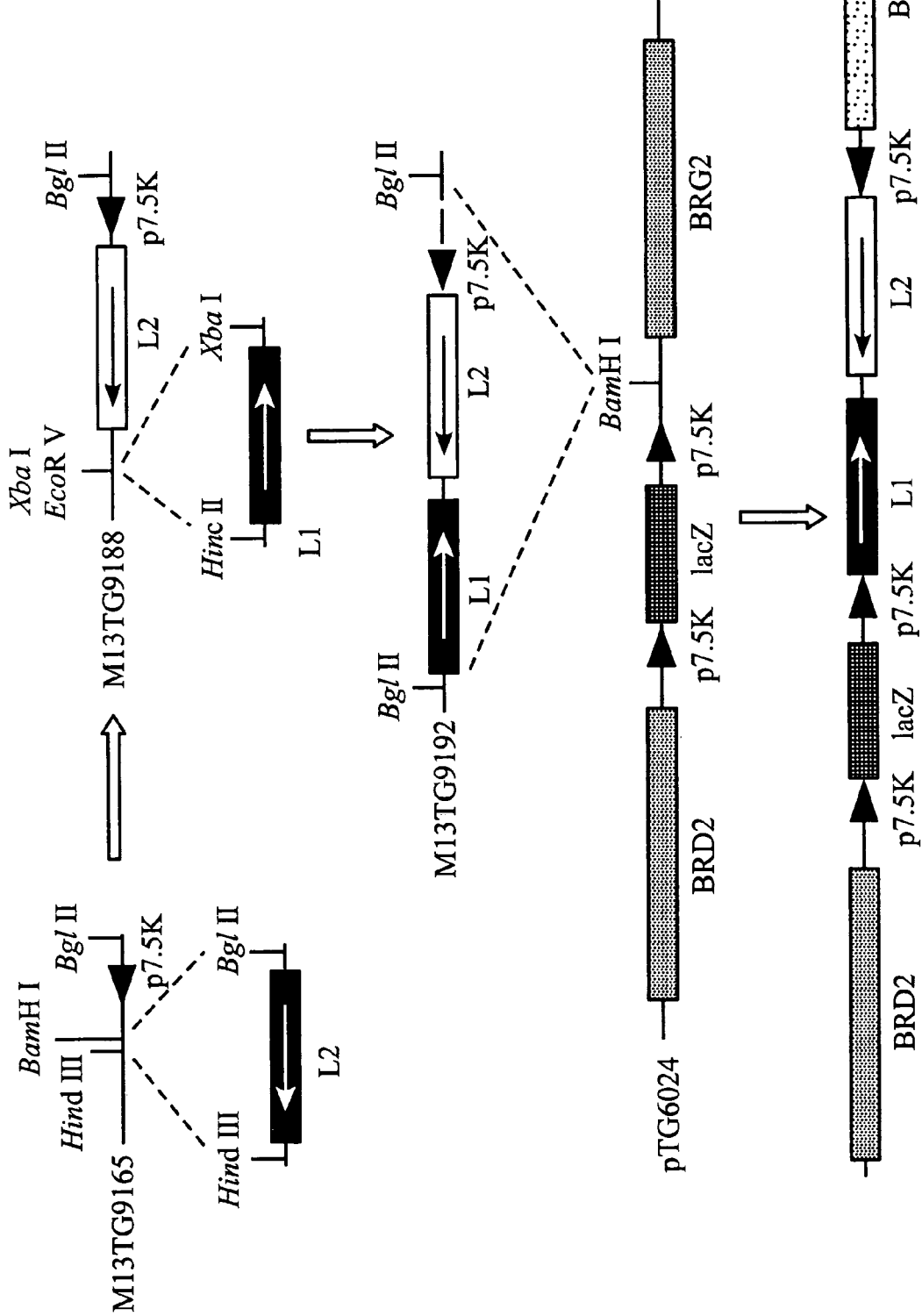

FIG. 3 diagrammatically illustrates the strategy which can be used to introduce the HPV-16 late genes L1 and L2 into the exclusion zone II of an MVA vaccinia virus, the left and right recombination arms being indicated (BRG2 and BRD2) respectively.

EXAMPLES

The present invention is described more fully with the aid of the following examples, without being limited as a result.

The constructions described below are carried out according to the general genetic engineering and molecular cloning techniques detailed in Maniatis et al., (1989, supra) or according to the manufacturer's recommendations when a commercial kit is used. Synthetic oligonucleotide site-directed mutagenesis in vitro is carried out with the aid of the kit distributed by Amersham. PCR amplification techniques are known to persons skilled in the art (see for example PCR Protocols—A guide to methods and applications, 1990, published by Innis, Gelfand, Sninsky and White, Academic Press Inc.). As regards the repair of restriction sites, the technique used consists in filling the protruding 5' ends with the aid of the large fragment of DNA polymerase I of E. coli (Klenow).

The cloning steps, the recombinant M13 bacteriophages are multiplied on the E. coli NM522 strain (Stratagene) in an agar-based minimum medium (7.5% agar) or in a liquid rich LBM medium. The recombinant plasmids carrying the ampicillin resistance gene are replicated in the E. coli strains C600.(Stratagene), BJ5183 (Hanahan, 1983, J. Mol. Biol. 166, 557-580) and NM522 on agar or liquid medium supplemented with 100 µg/ml of antibiotic. The BJ5183 strain is preferably used when the cloning is carried out by homologous recombination (Bubeck et al., 1993, Nucleic Acid Res. 21, 3601-3602).

The construction of the recombinant vaccinia viruses is carried out according to the conventional technology in the field which is disclosed in the documents already cited and in Mackett et al., (1982, Proc. Natl. Acad. Sci. USA 79, 7415-7419) and Mackett et al., (1984, J. Virol. 49, 857-864).

Example 1

Construction of the Copenhagen Vaccinia Virus VVTG5021&5065 Expressing the HPV-16 E6, E7, L1 and L2 Genes and the Human IL-2 Gene A. Isolation of the HPV16 L1 and L2 Genes The fragments coding for the L1 and L2 proteins are isolated by PCR from the genomic DNA of Caski cells (ATCC 1550) according to general prior art techniques. The fragment for amplification, carrying the L1 sequences, is subcloned into the vector M13TG130 (Kieny et al., 1983, Gene 26, 91-99) to give the construct M13TG8171. The sequence of the cloned L1 gene reveals several mutations compared with the sequence contained in Genebank (accession K02718): C in place of an A at position 248, C in place of an A at position 253, G in place of an A at position 537, G in place of a C at position 682, G in place of an A at position 874, insertion of a triplet ACT at position 1393, deletion of a triplet GAT at position 1390. The insertion of the PCR fragment, carrying the L2 sequences, into the vector M13TG6131 leads to M13TG9126. 5 point mutations are observed compared with the sequence disclosed in Genebank: C in place of a T at position 378, A in place of a G at position 691, A in place of a G at position 702, G in place of an A at position 990 and C in place of an A at position 1092. As a guide, the vector M13TG6131 is derived from M13TG131 (Kieny et al., 1983, supra) by mutation of the internal BglII site situated outside the multiple cloning sites.

B. Construction of the Vector pTG5021 for the Transfer of the L1 and L2 Genes into the TK Locus of the Genome of the Vaccinia Virus The gene coding for the L1 protein is modified by creating a BglII site upstream of the initiator ATG. The mutated gene is excized from the preceding vector (M13TG8185) by BglII-SacI digestion and inserted between the BamHI and SacI sites of pTG186-poly. The resulting construct is called pTG4019. The transfer vector pTG186-poly is described in detail in French Patent 2,583,429. It has 10 restriction sites for the insertion of the gene to be transferred and the promoter p7.5K for controlling its expression.

The gene coding for the L2 protein is isolated from M13TG9126 by BglII-HindIII digestion and then cloned between the BamHI and HindIII sites in 3' of the 7.5K promoter. M13TG9127 is obtained into which a SalI site is introduced upstream of the promoter by localized mutagenesis. The expression unit "p7.5K-L2 gene" is isolated from the mutated vector M13TG9129 and cloned into the SacI site of the transfer vector pTG4019 such that the two cassettes p7.5K-L1 and p7.5K-L2 are in opposite orientation. The construct thus obtained pTG5021 is represented in FIG. 1. The expression units are transferred into the genome of the Copenhagen strain of the vaccinia virus by homologous recombination. The recombinant virus designated VVTG5021 is isolated by selection with 5-bromodeoxyuridine (5BUDR).

C. Isolation of the HPV16 E6 and E7 Genes

The E6 and E7 genes are isolated from the Caski cell line as described in Examples 2 and 3 of European Patent EP 0,462, 187. Two constructs were derived from the clone M13E7/E6 containing the HPV-16 E6 and E7 genes so as to facilitate subsequent cloning steps. The first, designated M13TG8188, results from the introduction by site-directed mutagenesis of PstI and BamHI sites upstream and downstream, respectively, of the E7 gene, and the second, M13TG8189, comprises a PstI site upstream of the E6 gene. The introduction of point mutations upstream of an initiator ATG and downstream of a stop codon are within the capability of persons skilled in the art.

The combination of the HPV-16 E7 protein with the product of the retinoblastoma gene has been demonstrated by various authors (see for example Munger et al., 1989, EMBO J. 8, 4099-4105) and correlated with its transforming power. For obvious safety reasons, a nononcogenic mutant, from which the sequences coding for amino acids 21 to 26 of the native E7 protein which are involved in the transformation function have been deleted, is generated by site-directed mutagenesis of the vector M13TG8188 with the aid of the oligonucleotide oTG5118 (SEQ ID NO: 1). M13TG9104 is obtained. The mutated E7 gene is designated hereinafter E7*.

Likewise, it has been demonstrated that the HPV-16 E6 protein could interact with the product of expression of the tumor suppressor gene p53 (Crook et al., 1991, Cell 67, 547-556). The domain involved in this interaction has been clearly defined and is situated between residues 111 to 115 of the native protein. The vector M13TG9125 is generated by mutagenesis of M13TG8189 with the aid of the oligonucleotide oTG5377 (SEQ ID NO: 2). The mutated E6 gene is designated hereinafter E6*.

D. Construction of the Transfer Vector pTG5065 Carrying the HPV-16 E6 and E7 Genes and the Human IL-2 Gene Which are Integrated into the K1L Locus.

The 5.2 kb EcoRI K fragment of the left end of the Copenhagen vaccinia virus genome (Guillard et al., 1985, J. Virol. 53, 316-318) is cloned into the plasmid pUC8 (Gibco BRL)

linearized with EcoRI. The vector thus obtained is then subjected to controlled digestion with BglII followed by ligation so as to delete an 855 bp fragment coding for the K1L host restriction gene (Guillard et al., 1986, Proc. Natl. Acad. Sci., USA 83, 5573-5577). The 3.4 kb BglII fragment is isolated from this intermediate construct designated pUC8Khr and then cloned into the BamHI site of the plasmid pUC7 (Gibco BRL). pBACI is generated, into which an XhoI adaptor is introduced on the left of the unique BglII site. After digesting with XhoI and BglII, a SalI-BglII fragment carrying the p7.5K vaccinia promoter is inserted. The two EcoRI sites are removed by EcoRI digestion followed by treatment with Klenow and religation. The vector pTG2147 is obtained by introducing into the unique BglII site a multiple cloning site isolated from the vector p poly II (Lathe et al., 187, Gene 57, 193-201) isolated in the form of a BglII-BamHI fragment. It therefore comprises the recombination arms allowing insertion into the K1L locus surrounding the p7.5K promoter followed by the restriction sites.

The E6* and E7* genes are cloned downstream of the vaccinia promoter pH5R contained in the vector M13TG9132, to give M13TG9138 and M13TG9139, respectively. As a guide, the vector M13TG9132 comes from the insertion of the promoter of the H5R gene isolated by PCR from the viral genome into the phage M13TG6131.

Moreover, the cDNA coding for human interleukin-2 is isolated from the plasmid pTG36 (French Patent 2,583,770), introduced into an intermediate vector and taken out again by SalI-BamHI digestion so as to be inserted into the transfer vector pTG2147 targeting the locus K1L. The insertion is made at the level of the PstI and XbaI sites situated downstream of the promoter p7.5K, with the aid of cloning adaptors. pTG5056 is obtained.

The expression unit pH5R-E6* is isolated from the vector M13TG9139 in the form of a BglII-BamHI fragment which is introduced into the BamHI site of the vector pTG5056. The vector pTG5060 is generated. The expression unit pH5R-E7* is purified from M13TG9138 and inserted at the BamHI site of the vector pTG5060, to give pTG5062. It is indicated that insertion at the K1L locus leads to recombinant viruses having a replication capacity which is reduced or even destroyed in certain cell types. For these reasons, a positive selectable marker is introduced to facilitate identification of the recombinant viruses. The vector pTG5065 results from the cloning, into the BamHI site of pTG5062, of an expression cassette "pK1L-LacZ gene" isolated from the plasmid pIV75 (Chen et al., 1993, Virology 196, 682-693) by BglII-BamHI cleavage. As visualized in FIG. 2, it allows the transfer of the E6*, E7* and IL-2 units into the K1L locus of the vaccinia virus.

The recombinant vaccinia virus, called VVTG5065, is generated by homologous recombination after transfection of the vector pTG5065 into chicken embryo cells infected with the wild-type Copenhagen vaccinia and picked out by staining under agar with X-Gal. The vaccinia viruses VVTG5021 and VVTG5065 are used in double infection tests. The double recombinants are selected according to the two markers: formation of blue plaques in the presence of X-Gal and deletion of the TK marker. These, called VVTG5021&5065, express the units p7.5K-IL-2, pH5R-E6* and pH5R-E7* integrated at the K1L locus and the units p7.5K-L1 and p7.5K-L2 integrated at the TK locus.

The expression of the HPV genes can be verified by Western-blot analysis with the aid of appropriate monoclonal or polyclonal antibodies or by inverse PCR. The production of IL-2 can be-evaluated by ELISA test or by CTL test as described in the literature. As a guide, the level of expression in vitro is of the order of 60 ng/ml/$10^6$ cells infected with 1 pfu/cell and 24 h.

Example 2

Construction of the Copenhagen Vaccinia Virus Expressing the E6 and E7 Genes and the Human IL-2 Gene The cDNA coding for human interleukin-2 is isolated from the plasmid pTG36 by PstI digestion and inserted into the PstI site of the plasmid pTG186, giving PTG188. The virus obtained by homologous recombination is called VVTG188.

The E6* gene is isolated from M13TG9125 in the form of a PstI-BamHI fragment and inserted downstream of the 7.5K promoter between the PstI and XbaI sites of pTG2147 in the presence of a BamHI-XbaI adaptor, giving pTG5057. The E7* gene is placed under the control of the H5R vaccinia promoter producing M13TG9138 and the cassette bordered by the BamHI-BglII sites is subcloned into the BamHI site of pTG5057. pTG5059 is obtained, into whose BamHI site the LacZ selectable marker is inserted under the control of the promoter of the K1L vaccinia gene by BglII-BamHI digestion of the vector pIV75. The resulting construct is designated pTG5061 and the virus generated by homologous recombination with the vaccinia genome VVTG5061.

A recombinant vaccinia virus expressing the E6* and E7* genes integrated at the K1L locus and the human IL-2 gene integrated at the TK locus is obtained by co-infection of chicken embryo cells with the viruses VVTG5061 and VVTG188. As a guide, the latter produces a quantity of IL-2 approximately greater than 400 ng per $10^6$ cells infected at 1 pfu per cell for 24 h. The doubly recombinant virus is designated VVTG5061&188.

Example 3

Construction of a Copenhagen Vaccinia Virus Expressing the E6 and E7 Genes, and the Gene Coding for the Human Adhesion Cofactor B7.1

The cDNA coding for B7.1 is isolated from an mRNA preparation obtained from the Daudi cell line (ATCC CCL-213) by inverse PCR using the primers oTG6353 and oTG6352 (SEQ ID NO: 3 and 4). It is indicated that the sequence of the gene is disclosed in Genebank under accession number M27533. The amplified fragment is cloned between the BglII and EcoRI sites of M13TG6131 leading to M13TG9149 and then between the BamHI and EcoRI sites of pTG186. The construct is called pTG5090 and the virus obtained by homologous recombination VVTG5090. A vaccinia virus expressing the HPV-16 E6* and E7* genes integrated at the K1L locus and the human B7.1 gene integrated at the TK locus can be obtained by co-infection of chicken embryos with the viruses VVTG5061 and VVTG5090. The recombinant virus is designated VVTG5061&5090.

Example 4

Construction of an MVA Strain of a Vaccinia Virus Expressing the E6 and E7 Genes and the B7.1 Gene Integrated into the Zone of Excision III The MVA virus is derived from the Ankara strain of the vaccinia virus. It is not capable of generating infectious particles on mammalian cells but develops satisfactorily on chicken embryo fibroblasts. Its adaptation to these cells caused the excision of 6 regions which are not essential for its development and its infectious cycle on this type of cells (disappearance of about 15% of the viral genome; Meyer et al., 1991, J. Gen. Virol. 72, 1031-1038). Exogenous genetic material can be integrated at the level of any of these excision zones. Within the framework of the present invention, excisions II and III, which are located at the level of the HindIII restriction fragments N and A respectively, are used (Altenburger et al., 1989, Arch. Virol. 105, 15-27).

In a first instance, the vector pTG6019 allowing insertion into the excision zone III of the MVA virus is constructed. The homologous recombination arms on either side of the excision zone III are isolated by PCR from the viral genome (see American Patent U.S. Pat. No. 5,185,146) and the primers oTG7637 and oTG7638 (SEQ ID NO: 5 and 6) for the left arm and oTG7635 and oTG7636 (SEQ ID NO: 7 and 8) for the right arm. The amplified fragments are cloned into the EcoRI site of the vector pTG1E, to give pTG6019. The genetic material to be transferred is inserted between the two recombination arms. The vector pTG1E is similar to pTG1H (French Patent 2,583,429) except for the presence of an EcoRI adaptor in place of multiple cloning sites.

Firstly, a cassette for expression of the gus A marker gene is inserted. The 7.5K promoter is first cloned into the BamHI site of pTG6019. pTG6021 is obtained into whose BamHI site the gus A gene generated in the form of a BglII-BamHI fragment is inserted. This can be obtained from the sequence disclosed in the literature. The resulting construct is called pTG6022. The presence of the marker will make it possible to discriminate between the wild-type viruses and the recombinant viruses by detecting the GUS enzymatic activity with the substrate XglcA. A red color reveals the β-glucuronidase activity. However, for the purpose of a clinical application, it may be useful to be able to remove this bacterial marker from the final product after selection of the recombinant viruses. To do this, advantage is taken of the capacity of vaccinia to delete the sequences between two homologous sites. Accordingly, a second promoter p7.5K is inserted downstream of the gus A gene in a sense orientation relative to that which directs its expression. The vector pTG6022 is modified by insertion between the BamHI and SacI sites of a fragment p7.5K provided with cohesive ends, to give pTG6025.

The latter is completed by the insertion of the mutated E6* and E7* gene expression cassettes. A new promoter sequence p7.5K is first introduced, this time in antisense orientation relative to the preceding ones. This construct, called pTG6039, therefore comprises the labile GUS cassette "p7.5K→gus A-p7.5K→" followed by p7.5K in the opposite orientation. In parallel, the E6* and E7* genes are isolated from the vectors M13TG9104 and M13TG9125, respectively, by BamHI and PstI digestion and assembled in opposite orientation with respect to each other at the PstI site of M13TG6131. The whole is taken out in the form of a PstI fragment which is inserted into pTG6039 linearized with this same enzyme. The vector pTG6056 is obtained which contains the following sequences p7.5K→gus A-p7.5K→E7* -E6* ←p7.5K".

The inmunostimulatory gene B7.1 is integrated into the latter construct. To do this, the vector pTG6056 is cleaved with HindIII and KpnI before being ligated in the presence of the oligonucleotides oTG10451 and oTG10450 (SEQ ID NO: 9 and 10), to generate pTG6070. The latter will allow the cloning of the expression cassette "pH5R-B7.1" by homologous recombination. To this effect, the B7.1 sequences isolated from M13TG9149 are cloned downstream of the vaccinia promoter pH5R, to form M13TG9184. The BglII-EcoRI fragment carrying the cassette is integrated into the vector pTG6070 linearized with XhoI by homologous recombination in E. coli. The vector pTG6079 is obtained which in total comprises the gus A marker gene in a "labile" form and the cassettes for expression of the HPV-16 early genes as well as a cassette for the costimulation gene B7.1. The virus generated by homologous recombination with the MVA genome is designated MVATG6079.

The units for expression of the HPV-16 late genes can be inserted into the excision zone II with the aid of the transfer vector pTG6018. It is constructed by inserting into the EcoRI site of pTG1E left and right recombination arms bordering the II excision, which are generated by PCR using the primers oTG7665 and oTG7584 (SEQ ID NO: 11 and 12) and. oTG7639 and oTG7640 (SEQ ID NO: 13 and 14). As above, a cassette for expression of a positive marker is integrated between the two arms in order to facilitate the detection of the recombinant viruses, it being possible to remove it after the selection step (Spehner et al., 1990, J. Virol. 64, 527-533). The vector pTG6020 results from the cloning of the LacZ gene placed downstream of the promoter p7.5K into the vector pTG6018 linearized with BamHI. pTG6020 is modified by inserting a sequence p7.5K between its BamHI and SacI sites situated downstream of the LacZ gene. pTG6024 is obtained. The cassettes L1 and L2 can then be introduced according to a strategy as shown in FIG. 3.

Example 5

Construction of an MVA Strain of Vaccinia Virus Expressing the E6 and E7 Genes, and the IL-2 Gene Integrated into the Excision Zone III The same strategy as above is used to introduce the IL-2 gene into the vector pTG6056. After cloning the recombinant oligonucleotides oTG10503 and oTG10502 (SEQ ID NO: 15 and 16) to produce pTG6076, the latter is cleaved with XhoI and the BglII-EcoRI fragment is prepared from M13TG9185 (pH5R-IL-2) inserted by homologous recombination. The vector pTG6090 thus obtained comprises the gus A marker gene in a "labile" form, the cassettes for expression of the. HPV-16 early genes as well as a human IL-2 gene cassette. The recombinant virus obtained by homologous recombination with the MVA genome is designated MVATG6090. The late genes can be integrated into the excision zone II using pTG6018, as indicated above.

Example 6

Validation of the Vector VVTG5021&5065 in an Animal Model

A. Toxicity Studies

Nude mice received $10^7$ pfu of VVTG5021&5065 or $10^7$ pfu of wild-type vaccinia virus by the intravenous, intramuscular, subcutaneous or intracranial route. Groups of 5 mice were formed depending on the type of virus injected and the route of administration and the number of animals having lesions linked to vaccinia was evaluated 26 days after the injection. The mice which received the recombinant virus showed no lesion regardless of the route of administration used, whereas the majority of the animals treated with the wild-type vaccinia have lesions whose frequency and seriousness depends on the route of administration. Furthermore, deaths are recorded in the case of an intravenous and intracranial injection. These data show that VVTG5021&5065 is attenuated compared with the wild-type virus and that it does not cause lesions even after an intracranial injection.

B. Immunoprophylaxy Experiments with VVTG5021&5065

C57BL6 mice were vaccinated three times by the subcutaneous route with $10^7$ pfu of VVTG5021&5065. Three days after the last immunization, these animals are challenged with $10^3$ E7W1 cells implanted subcutaneously. As a guide, the E7W1 cells are obtained from a murine lymphoma line transfected with a vector expressing the HPV-16 oncogenic E7 gene. The percentage survival of the animals as a function of time is compared to that obtained with control mice treated with $10^7$ pfu of a nonrecombinant vaccinia virus VVTG186 (derivative of the TG186 vector described above). Monitoring of mortality shows a difference between the two groups. In the control group, 100% of the animals died at D36 whereas 40% of the animals vaccinated with VVTG5021&5065 were still alive at D36 and more than 30% at D51.

Thus, the recombinant viruses expressing HPV antigens and an immunostimulatory gene exhibit antitumor activity against tumor cells expressing the HPV-16 E7 oncogene.

C. Immunotherapy Experiments.

C57BL6 mice are inoculated with $10^3$ E7W1 cells implanted subcutaneously (D0). $10^7$ pfu of recombinant viruses are then administered, also subcutaneously at D3 and then D6 and finally D9 and the percentage survival of the animals is determined compared with the control animals which received a nonrecombinant virus. Whereas 100% of the control animals died, a notable increase in the survival of the animals injected with a mixture of VVTG5061§5021 and VVTG188 is observed. Similar results are obtained after administration of VVTG5065§5021 and VVTG188.

These immunotherapy experiments were repeated using a different tumor model, BMK16myc cells replacing the E7w1 cells. The BMK16myc cells are kidney cells from newborn mice transfected with the HPV-16 genome and the murine c myc gene. The animals are treated with $10^7$ MVATG6090 viruses expressing the HPV-16 E6* and E7* genes and the human IL-2 gene. Compared with the controls, the treated mice exhibit a delayed tumor growth up to D15.

The invention claimed is:

1. A composition consisting of a recombinant vector into which is inserted DNA sequences coding for (i) the early E6 polypeptide of a papillomavirus; (ii) the early E7 polypeptide of a papillomavirus; (iii) the late L1 polypeptide of a papillomavirus; (iv) the late L2 polypeptide of a papillomavirus; and (v) a polypeptide having an immunostimulatory activity;

wherein each of said DNA sequences is placed under the control of the independent elements necessary for its expression in a host cell or organism;

wherein said polypeptide having an immunostimulatory activity is selected from the group consisting of interleukin-2, interleukin-7, and the co-adhesion molecule B7.2; and wherein said recombinant vector is provided in combination with a pharmaceutically acceptable carrier.

2. The composition of claim 1, wherein the polypeptide having an immunostimulatory activity is interleukin-2.

3. The composition of claim 1, consisting of one recombinant viral vector in the genome of which is inserted a DNA sequence coding for the E6 polypeptide of a papillomavirus; a DNA sequence coding for the E7 polypeptide of a papillomavirus; a DNA sequence coding for the L1 polypeptide of a papillomavirus; a DNA sequence coding for the L2 polypeptide of a papillomavirus; and a DNA sequence coding for interleukin-2;

wherein said DNA sequence coding for the E6 polypeptide of a papillomavirus, said DNA sequence coding for the E7 polypeptide of a papillomavirus, and said DNA sequence coding for interleukin-2 are inserted within one locus of said genome; and wherein said DNA sequence coding for the L1 polypeptide of a papillomavirus and said DNA sequence coding for the late L2 polypeptide of a papillomavirus are inserted within a different locus of said genome.

4. The composition of claim 3, wherein said E6 or E7 or both E6 and E7 polypeptides are, respectively nononcogenic variants of the native E6 and E7 polypeptides of a human papillomavirus;

wherein said nononcogenic variant of the E6 polypeptide is the native HPV-16 E6 polypeptide deleted of amino acids 111-115; and wherein said nononcogenic variant of the E7 polypeptide is the native HPV-16 E7 polypeptide deleted of amino acids 21-26.

5. A method for the treatment of dysplasia or cancer of the neck of the uterus, comprising administering an effective amount of the composition of claim 1 to a patient in need of such treatment.

6. A method for the treatment of a papillomavirus infection, comprising administering an effective amount of the composition of claim 1 to a patient in need of such treatment.

7. The composition of claim 1, wherein said elements necessary for the expression of the DNA sequences comprise a promoter selected from the group consisting of the CMV promoter and the promoters of the thymidine kinase (TK), 7.5K, H5R and K1L genes.

8. A composition consisting of a recombinant vector into which is inserted DNA sequences coding for (i) the early E6 polypeptide of a papillomavirus; (ii) the early E7 polypeptide of a papillomavirus; and (iii) a polypeptide having an immunostimulatory activity;
   wherein each of said DNA sequences is placed under the control of the independent elements necessary for its expression in a host cell or organism;
   wherein said polypeptide having an immunostimulatory activity is selected from the group consisting of interleukin-2, interleukin-7, and the co-adhesion molecule B7.2; and
   wherein said recombinant vector is provided in combination with a pharmaceutically acceptable carrier.

9. The composition of claim 8, wherein said elements necessary for the expression of the DNA sequences comprise a promoter selected from the group consisting of the CMV promoter and the promoters of the thymidine kinase (TK), 7.5K, H5R and K1L genes.

10. The composition of claim 8, wherein the polypeptide having an immunostimulatory activity is interleukin-2.

11. The composition of claim 8, wherein said papillomavirus polypeptide is the E6 or the E7 or the E6 and E7 polypeptide of a human papillomavirus.

12. The composition of claim 8, consisting of one recombinant viral vector into the genome of which is inserted within the same locus a DNA sequence coding for the E6 polypeptide of HPV-16, a DNA sequence coding for the HPV-16 E7 polypeptide and a DNA sequence coding for interleukin-2.

13. The composition of claim 8,
   wherein said E6 or E7 or both E6 and E7 polypeptides are, respectively, nononcogenic variants of the native E6 and E7 polypeptides of a human papillomavirus;
   wherein said nononcogenic variant of the E6 polypeptide is the native HPV-16 E6 polypeptide deleted of amino acids 111-115; and
   wherein said nononcogenic variant of the E7 polypeptide is the native HPV-16 E7 polypeptide deleted of amino acids 21-26.

14. A method for the treatment of dysplasia or cancer of the neck of the uterus, comprising administering an effective amount of the composition of claim 8 to a patient in need of such treatment.

15. A method for the treatment of a papillomavirus infection, comprising administering an effective amount of the composition of claim 13 to a patient in need of such treatment.

* * * * *